(12) United States Patent
Massaro et al.

(10) Patent No.: US 10,568,308 B2
(45) Date of Patent: Feb. 25, 2020

(54) SYSTEMS AND METHODS FOR MOBILE AUTOMATED MASS RELEASE OF INSECTS

(71) Applicant: Verily Life Sciences LLC, Mountain View, CA (US)

(72) Inventors: Peter Massaro, Belmont, CA (US); Robert Sobecki, Brisbane, CA (US); Brian Wasson, Oakland, CA (US); Charles Behling, Mountain View, CA (US); Gabriella Levine, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 15/413,564

(22) Filed: Jan. 24, 2017

(65) Prior Publication Data
US 2018/0206464 A1    Jul. 26, 2018

(51) Int. Cl.
*A01M 99/00* (2006.01)
*A01K 67/033* (2006.01)
*A01K 29/00* (2006.01)
*G05D 7/06* (2006.01)

(52) U.S. Cl.
CPC .......... *A01K 67/033* (2013.01); *A01K 29/005* (2013.01); *A01M 99/00* (2013.01); *G05D 7/0605* (2013.01); *A01M 2200/012* (2013.01)

(58) Field of Classification Search
CPC ... A01K 67/033; A01K 29/005; A01M 99/00; A01M 2200/012; G01F 1/661; G01F 1/663; G01F 1/666
USPC ................... 239/152; 119/174, 843, 6.5, 6.6
See application file for complete search history.

(56) References Cited

U.S. PATENT DOCUMENTS

| 3,468,289 | A | * | 9/1969 | Broida | ................... B65D 25/14 |
| | | | | | 119/496 |
| 3,871,330 | A | * | 3/1975 | Swanson | .............. A01K 67/033 |
| | | | | | 119/6.5 |
| 4,572,427 | A | * | 2/1986 | Selfridge | ................. A01C 1/02 |
| | | | | | 165/146 |
| 4,594,964 | A | * | 6/1986 | Vargas | ................. A01K 67/033 |
| | | | | | 119/6.6 |

(Continued)

FOREIGN PATENT DOCUMENTS

| WO | 2009067089 | 5/2009 |
| WO | 2016088129 | 6/2016 |

OTHER PUBLICATIONS

International Application No. PCT/US2018/014154, "International Search Report and Written Opinion", dated Jun. 27, 2018, 11 pages.

(Continued)

*Primary Examiner* — Chee-Chong Lee
(74) *Attorney, Agent, or Firm* — Kilpatrick Townsend & Stockton LLP

(57) ABSTRACT

Systems and methods for automated release of insects are disclosed. In one embodiment, a system includes: an insect storage device defining one or more internal compartments to store a population of insects; a loading mechanism for loading the insect storage device with a population of insects; and an insect release device coupled to the loading mechanism and configured to release into an environment one or more insects from the population of insects in the insect storage device.

9 Claims, 4 Drawing Sheets

(56) References Cited

U.S. PATENT DOCUMENTS

| | | | | |
|---|---|---|---|---|
| 4,765,274 A * | 8/1988 | Pizzol | ............... | A01K 67/033 |
| | | | | 119/6.6 |
| 4,850,305 A * | 7/1989 | Georgi | ............... | A01K 67/033 |
| | | | | 119/303 |
| 5,113,799 A * | 5/1992 | Carr | ............... | A01K 67/033 |
| | | | | 119/6.5 |
| 5,123,201 A * | 6/1992 | Reiter | ............... | A01M 1/026 |
| | | | | 43/107 |
| 5,148,989 A | 9/1992 | Skinner | | |
| 6,089,477 A | 7/2000 | Dillon | | |
| 6,937,156 B2 | 8/2005 | Gardner, Jr. et al. | | |
| 8,408,164 B2 * | 4/2013 | Robinson, Jr. | ....... | A01K 67/033 |
| | | | | 119/174 |
| 8,967,029 B1 | 3/2015 | Calvert et al. | | |

OTHER PUBLICATIONS

International Application No. PCT/US2018/014154 , "Invitation to Pay Additional Fees and Partial Search Report", dated Apr. 27, 2018, 2 pages.

U.S. Appl. No. 15/701,933 , "Non-Final Office Action", dated Apr. 11, 2018, 26 pages.

U.S. Appl. No. 15/701,933 , "Final Office Action", dated Oct. 29, 2018, 24 pages.

International Application No. PCT/US2018/014154 , "International Preliminary Report on Patentability", dated Aug. 8, 2019, 8 pages.

U.S. Appl. No. 15/701,933 , "Non-Final Office Action", dated Jun. 7, 2019, 28 pages.

\* cited by examiner

SYSTEMS AND METHODS FOR MOBILE AUTOMATED MASS RELEASE OF INSECTS

BACKGROUND

All continents except Antarctica suffer from the plague of mosquito-vectored diseases. Various techniques for the control of mosquito populations involve the generation of sterile male insects for release into the wild for mating with local females. These techniques require systems for releasing the reared insects into the wild.

SUMMARY

In one embodiment, a system of the present disclosure may comprise: an insect storage device defining one or more internal compartments to store a population of insects; a loading mechanism for loading the insect storage device; and an insect release device coupled to the loading mechanism and configured to release into an environment one or more insects from the population of insects in the insect storage device.

Another embodiment of the present disclosure may comprise: a tube defining one or more compartments for storing mosquitos; a loading mechanism configured to reposition the one or more compartments; a blower positioned to apply air pressure to a portion of the tube to force mosquitos to exit the tube; and a processor communicatively coupled to the loading mechanism and the blower and configured to control the loading mechanism and the fan.

Another embodiment of the present disclosure may comprise a method comprising: receiving a location signal from a location sensor; receiving a rate signal from a sensor that detects a rate of insect release; controlling a loading mechanism and an insect release device based on the location signal and rate signal to release a population of insects into an environment from the insect release device.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

DETAILED DESCRIPTION

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of Automated Mass Release of Insects

A commercial rearing program may raise modified mosquitos for use in controlling a local mosquito population. For example, the rearing program may engineer mosquitos with desirable traits. These desirable traits may include sterility (or otherwise lacking the ability to produce viable offspring) and capable of competing with wild-type insects of the same species. In some embodiments, the reared insects may be male insects, e.g., sterile male mosquitos that are able to compete with wild mosquitos in the area for mating partners. Other desirable traits may include, for example, longevity, size, flight capability, and/or heat-resistance. Once reared these modified mosquitos must be released into the wild to compete with local mosquitos for mating partners. Embodiments of the present disclosure provide systems and methods for release of insects.

One illustrative embodiment of the present disclosure includes an insect storage device, a loading mechanism, and an insect release device. In the illustrative embodiment, the insect storage device is a tube having multiple internal dividers. Each of the dividers forms an enclosed area within the tube. These enclosed areas can be used to store insects, e.g., one or more species of mosquitos.

The illustrative embodiment further includes a loading mechanism that moves the plurality of dividers to expose the compartments to an opening to allow the insects to fly out of the insect storage device. For example, in the illustrative embodiment, each of the plurality of dividers may be interconnected, and the loading mechanism may comprise an electric motor or solenoid configured to move the dividers forward or backward. In the illustrative embodiment, the loading mechanism positions the chamber created by the dividers opposite an opening in the tube (e.g., the chamber is positioned such that it is open). This opening is opposite to an insect release device. In the illustrative embodiment, the insect release device comprises a fan configured to blow air through the enclosure formed by dividers and out the opening. This forces the insects (e.g., the mosquitos) out of the opening to release them into an environment. Further, in some embodiments, the loading mechanism comprises a hopper comprising a plurality of insect storage devices (e.g., tubes). In such an embodiment, the loading mechanism may be configured to sequentially load the plurality of insect storage devices.

In the illustrative embodiment, the loading mechanism (e.g., the electric motor or solenoid) and the insect release device (e.g., the fan) are both controlled by a processor. The processor is configured to vary the rate of movement of the loading mechanism and the amount of air moved by the fan.

In the illustrative embodiment the processor is further coupled to one or more sensors. For example, in one embodiment, the one or more sensors comprises a location sensor (e.g., a GPS, AGPS, or GLONASS receiver) configured to determine the current location of the insect release system. The processor may control the operation of the loading mechanism and the insect release device based in part on these signals. Further, in some embodiments, the processor is coupled to one or more additional sensors configured to determine the rate of insect release or the number of insects that have been released. The processor may further control the operation of the loading mechanism and the insect release device based in part on these signals. For example, the processor may be pre-programmed to release a certain number of insects in specific locations. Further, in some embodiments, the processor may be pre-programmed to release a certain number of insects at known intervals.

In some embodiments, the entire insect release system may fit on a vehicle, for example, a car, truck, boat, or aircraft (e.g., airplane, helicopter, or drone). Further in some embodiments, the entire insect release system may be mounted to a drone, which is configured to fly to certain locations and release predetermined numbers of mosquitos. In still other embodiments, the insect release system may be configured to be carried by a person (e.g., in a backpack) or mounted to a bicycle.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Illustrative Systems for Automated Mass Release of Insects

Figure 1:
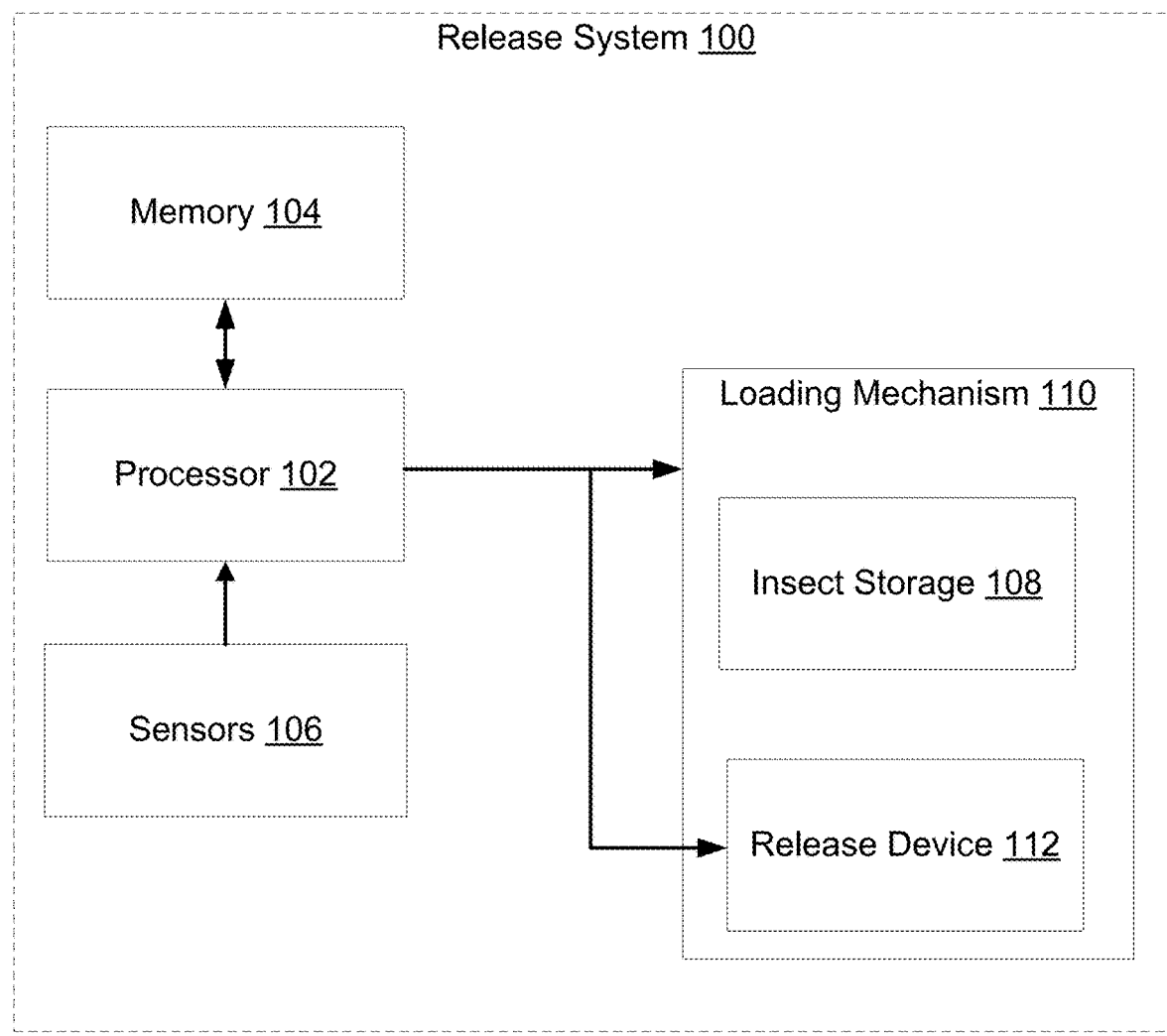
FIG. 1 shows an illustrative system for mobile automated mass release of insects according to an embodiment of the present disclosure.

FIG. 1 shows an illustrative release system 100 for automated mass release of insects. As shown in FIG. 1, the release system 100 comprises a processor 102, memory 104, sensors 106, insect storage 108, loading mechanism 110, and release device 112.

As shown in FIG. 1, the processor 102 may comprise one or more of a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The processor 102 may comprise or be in communication with memory 104, which may comprise, e.g., ROM, RAM, ASIC, a floppy disk, CD-ROM, magnetic disk, memory chip, configured processor, all optical media, all magnetic tape or other magnetic media comprising executable program code. The memory 104 may comprise machine readable program code, which is executed by processor 102 to perform functions, e.g., for location detection or for controlling release of insects. Further, the processor 102 may store data, e.g., data recorded from sensor 106 in memory 104.

In some embodiments, processor 102 may be coupled to a user interface device. In some embodiments, the user interface device may comprise a control box, e.g., a box with user interface devices, e.g., buttons, sliders, touchpad, touch-screen, display, etc. for use in controlling the rate of release of the release system 100. Further, in some embodiments, processor 102 may be coupled to a network interface (e.g., a modem, a network interface (wireless, wired, both, or other combination thereof), an infrared communication device, a wireless communication device, and/or a chipset (such as a Bluetooth™ device, an Institute of Electrical and Electronics Engineers (IEEE) 802.11 device (e.g., a device utilizing one or more of the IEEE 802.11 standards described herein), a WiFi device, a WiMax device, cellular communication facilities, etc.), to enable the processor to be controlled by a separate device, e.g., a smartphone, tablet, laptop, desktop, server, or other computer.

Release system 100 further comprises one or more sensors 106. In some embodiments, sensors 106 may comprise location sensors, e.g., a GPS, AGPS, or GLONASS receiver. Further, in some embodiments, the sensors 106 may comprise one or more sensors to detect the number of insects in insect storage 108, the rate of insects leaving insect storage 108, and/or the number of insects that have left insect storage 108. For example, in some embodiments, sensors 106 may comprise one or more of: a weight sensor, a camera, a microphone, an ultrasonic Doppler sensor, or a light sensor. For example, in one embodiment, one or more of these sensors may be mounted to the insect storage 108 and/or release device 112, and configured to measure the number of insects exiting an opening in insect storage 108.

Insect storage 108 comprises a compartment configured to store one or more types of mosquitos. For example, in some embodiments, insect storage 108 may comprise a tube, e.g., a round, square, or some other cross-section, tube. In some embodiments, insect storage 108 further comprises a plurality of dividers arranged to create one or more internal compartments in insect storage 108. In some embodiments, these dividers may comprise sections and subsections configured to provide one or more internal compartment for storing insects. In some embodiments, the dividers my comprise a plastic material comprising surfaces on which the insects may roost. In some embodiments, the material may be selected to provide better roosting areas. Examples of some materials that may be used for forming dividers in the insect storage 108 comprise: mesh, sandblasted plastic, Teflon, foam, or perforated steel. Further, in some embodiments, each of the dividers is interconnected and configured to move within insect storage 108. In some embodiments, there may be a plurality of insect storage devices, e.g., a plurality of tubes of mosquitos, each comprising a plurality of dividers forming separate compartments. Further, in some embodiments, loading mechanism 110 may further comprise compartments for feeding and air circulation to help maintain the fitness of the insects. For example, a compartment for feeding may comprise a compartment for sugar feeding, e.g., an area for positioning a sugar coated cotton material (e.g., at the center of the cartridge) so insects can feed during transport.

Loading mechanism 110 comprises a device configured to load insect storage 108 into position to release insects. For example, in some embodiments, loading mechanism 110 may comprise a solenoid, electric motor, pneumatic cylinder, or some other device for moving insect storage 108 or for moving dividers within insect storage 108. Further, in some embodiments, the loading mechanism 110 comprises a hopper comprising a plurality of insect storage devices 108. In such an embodiment, the loading mechanism 110 may be configured to sequentially load the plurality of insect storage devices 108.

Release device 112 comprises a system for removing insects from insect storage 108. For example, in one embodiment, each of the plurality of dividers may be interconnected, and the loading mechanism 110 may comprise an electric motor or solenoid configured to move the dividers forward or backward within the tube. In the illustrative embodiment, the loading mechanism 110 positions the chamber created by the dividers such that the chamber is opposite to an opening in the tube. The opening is opposite to an insect release device 112, in the form of a fan configured to blow air through the enclosure formed by dividers and out the opening. This forces the insects (e.g., the mosquitos) out of the opening to release them into an environment. In other embodiments, release device 112 may comprise a different source of force, e.g., a nozzle for the release of compressed air, carbon dioxide, or some other substance to propel insects out of insect storage 108.

In some embodiments, the loading mechanism 110 may be configured to change the size of the opening in insect storage 108 that is exposed to release device 112. In some embodiments, this enables the release system 100 to release insects at a controllable rate. In some embodiments, a processor may determine the rate based in part on data received from sensor 106. For example, sensor 106 may comprise a GPS sensor, and the rate of release may be determined based in part on the location of the release system 100. Further, in some embodiments, sensor 106 may further comprise a sensor configured to determine a current rate of release. In some embodiments, the loading mechanism 110 may control the current rate of release to match a desired rate of release, e.g., a predetermined desired rate of release.

Further, in some embodiments the insect storage 108 further comprises an array of conductors electrically coupled to a power source. Each of these conductors may be positioned at a predetermined distance from an electrical ground. This predetermined distance may correspond to the size of an insect, e.g., a mosquito. Thus, when a mosquito roosts on one of the conductors the mosquito may complete the circuit, allowing voltage and/or current to flow through the mosquito. In some embodiments, a measurement circuit may measure the conducted voltage and/or current to determine that a mosquito is present and other information about the mosquito (e.g., its size, species, gender, etc.). Further, in some embodiments, a higher voltage and/or current may be supplied to trigger the mosquito to loft. In some embodiments, this may increase the likelihood that each insect in insect storage 108 is forced out into the environment.

Figure 2A:
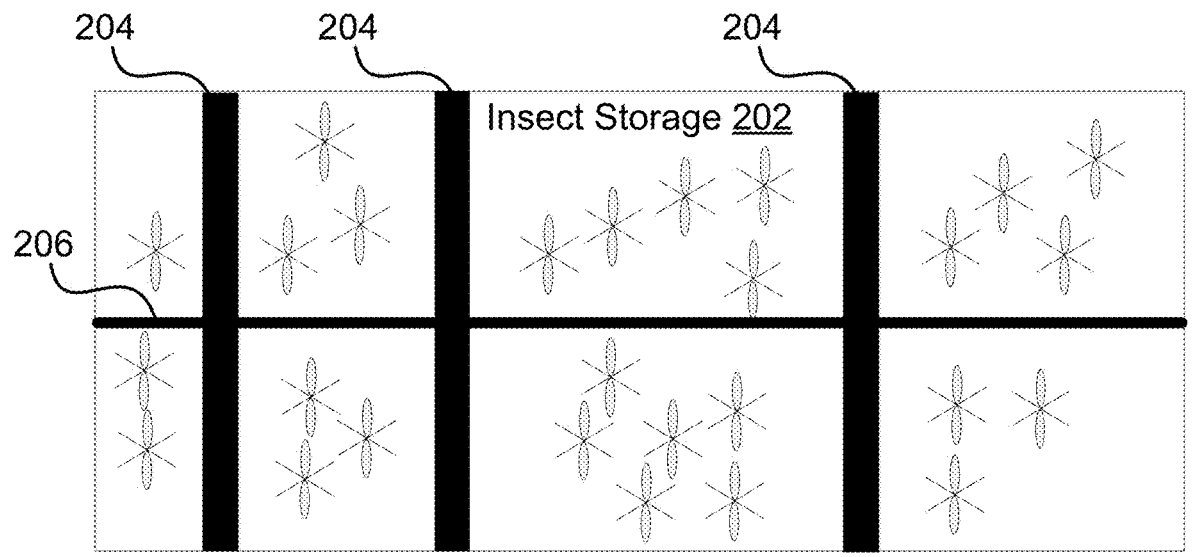
FIG. 2A shows another illustrative system for mobile automated mass release of insects according to an embodiment of the present disclosure.

Turning now to FIG. 2A, FIG. 2A comprises an example insect storage container 202. As shown in FIG. 2A, the insect storage container 202 comprise a plurality of dividers 204 that create a plurality of enclosed areas. In some embodiments, each of these enclosed areas may be of a different size. Each of these enclosed areas includes one or more insects, which may comprise one or more species of mosquitos. In some embodiments, each of the enclosed areas may comprise different numbers, types, or genders of insects. Further, each of the dividers is interconnected by a shaft 206. In some embodiments, the loading mechanism 110, discussed above, may move this shaft forward or backward, thus moving the location of each compartment within insect storage 202.

Figure 2B:
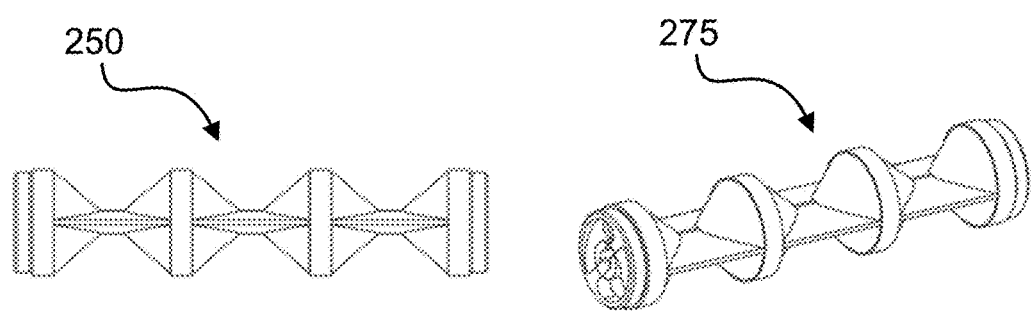
FIG. 2B shows another illustrative system for mobile automated mass release of insects according to an embodiment of the present disclosure.

Turning now to FIG. 2B, which shows additional example perspectives of dividers 250 and 275 that may be found in insect storage 202. As shown in FIG. 2B, each of the dividers comprises areas on which one or more mosquitos may roost. Further, each divider is interconnected, and thus may be pushed forward or backward together. In some embodiments, the dividers may further comprise compartments for sugar feeding and air circulation to help maintain the fitness of the insects. In some embodiments, the dividers 250 and 275 are constructed of material to provide roosting space for insects. Some example materials for dividers include: mesh, sandblasted plastic, or perforated steel.

The embodiments shown in FIG. 2B are examples. In other embodiments, different shapes and/or form factors may be used to maximize one or more of: roosting area, air flow, storage space, and/or ability to release insects without damage (e.g., with comparatively less pressure from release device 112).

Figure 3:
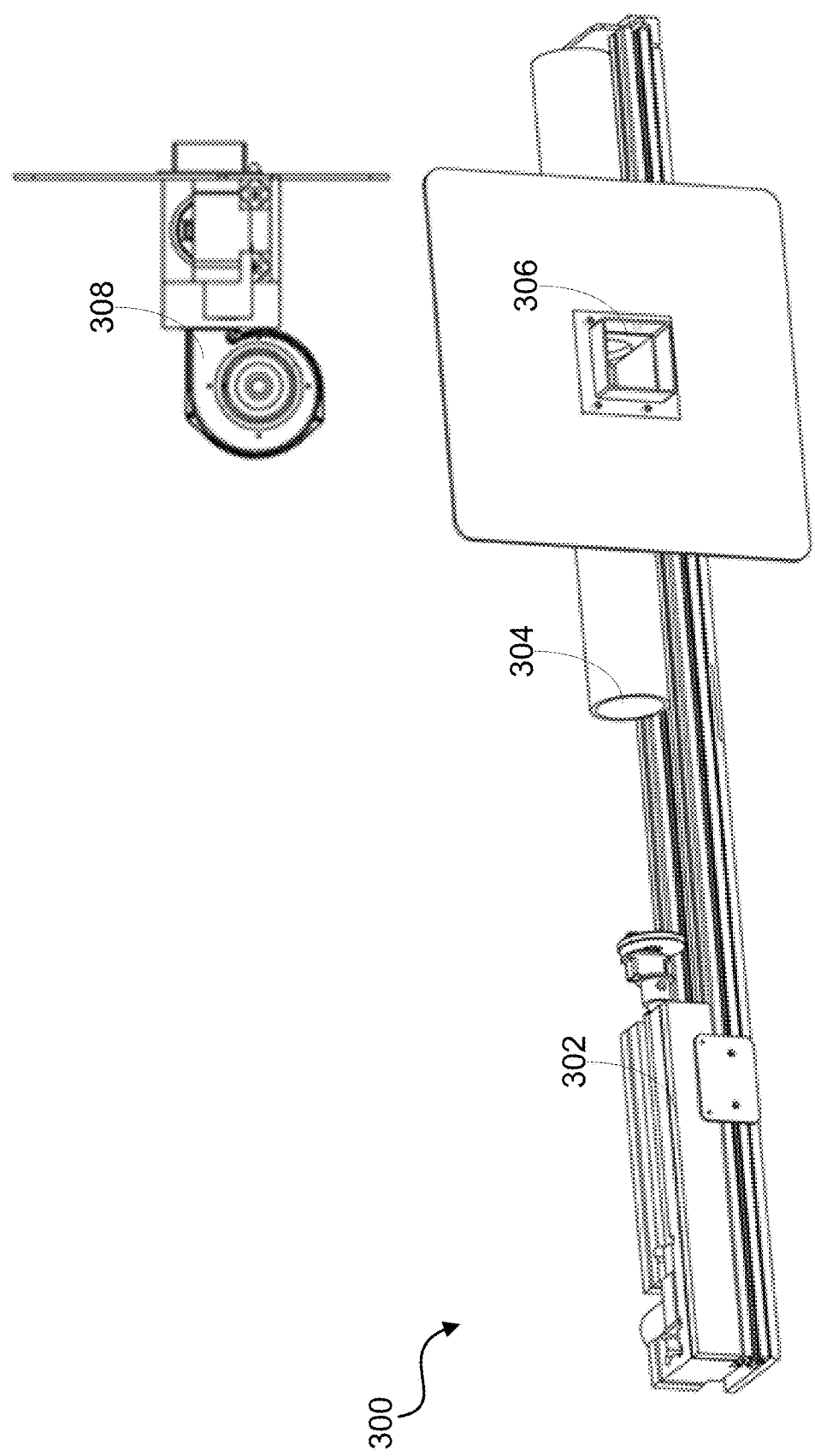
FIG. 3 shows another illustrative system for mobile automated mass release of insects according to an embodiment of the present disclosure.

Turning now to FIG. 3, which shows an example system 300 for automated mass release of insects. The system 300 shows one example embodiment of a loading mechanism 302, insect storage 304, and release mechanism 306.

As shown in FIG. 3, the loading mechanism 302 comprises a mechanism, such as a piston or solenoid to push or pull on a structure (e.g., one of the structures described above with regard to FIG. 2A or 2B) that may be positioned inside insect storage 304 to create enclosures for storing insects. The loading mechanism pushes the structure into a position such that the chamber it creates is positioned opposite (e.g., in front of) opening 306.

The opposite side of opening 306 includes blower 308, which is shown in a perspective view. The blower 308 may comprise one or more types of electric fans, e.g., a box fan, axial fan, centrifugal fan, radial fan, cross flow fan, bellows, or any other system known in the art for generating an air pressure differential. The blower 308 provides air pressure that forces insects out of the insect storage 304 via opening 306. In other embodiments, additional forms of pressure may be used, e.g., compressed air or carbon dioxide, or some other type of compressed gas to provide pressure to force insects out of insect storage 304.

Illustrative Methods for Automated Mass Release of Insects

Figure 4:
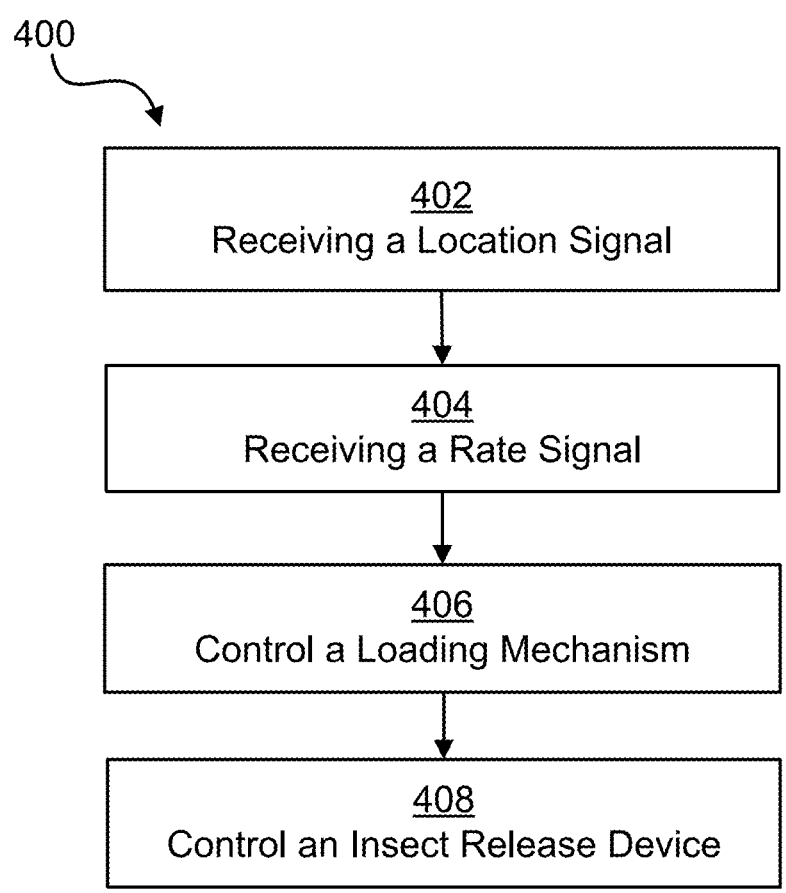
FIG. 4 is a flow chart for a method for mobile automated mass release of insects according to an embodiment of the present disclosure.

FIG. 4 is a flow chart for a method of automated mass release of insects according to one embodiment. In some embodiments, the steps in FIG. 4 may be implemented in program code executed by a processor. In some embodiments, these steps may be implemented by a group of processors. In some embodiments the steps shown in FIG. 3 may be performed in a different order. Alternatively, in some embodiments, one or more of the steps shown in FIG. 4 may be skipped, or additional steps not shown in FIG. 4 may be performed. The steps below are described with reference to components described above with regard to system 100 shown in FIG. 1 and/or the system 202 shown in FIG. 2A.

The method 400 begins at step 402 when processor 102 receives a location signal from one or more sensors 106. For example, in one embodiment, the one or more sensors comprises a location sensor (e.g., a GPS, AGPS, or GLONASS receiver) configured to determine the current location of the insect release system. Further, in some embodiments, the sensors 106 may further comprise an accelerometer and/or velocity sensor from which the processor 102 may determine a current location. The processor 102 may use this location to determine whether to release insects at that location. For example, the processor 102 may be preprogrammed to release mosquitos at certain known locations (e.g., areas that have a mosquito infestation or an outbreak of mosquito vectored diseases).

Next at step 404 the processor 102 receives a rate signal from sensor 106. For example, in some embodiments, sensors 106 may comprise one or more of: a weight sensor, a camera, a microphone, an ultrasonic Doppler sensor, or a light sensor. For example, in one embodiment, one or more of these sensors may be mounted to the insect storage 108 and/or release device 112, and configured to measure the number of insects exiting an opening in insect storage 108.

For example, in one embodiment, the sensor 106 comprises a light source and a light detector at an opening of the insect storage 108. When an insect crosses the light beam the sensor may transmit a signal that processor 102 uses to detect that an insect has left insect storage 108.

Then at step 406 the processor 102 controls a loading mechanism 110. In one embodiment, based on a determined location or a number of released mosquitos the processor 102 may control the loading mechanism to reposition the insect storage 108 (e.g., reposition the tube) or components within the insect storage 108 (e.g., dividers within the insect storage 108). In still other embodiments, loading mechanism 110 may load a new insect storage container (e.g., a second tube after all the insects in a first tube have been released).

Next at step 408 the processor 102 controls a release device 112. In one embodiment, based on a determined location or a number of released mosquitos the processor 102 may change the amount of power applied to release device 112 (e.g., to increase or decrease the air pressure provided by a fan) to increase or decrease the rate at which insects are released. For example, the processor 102 may be programmed to release a certain number of insects at specific locations. Thus, when at one of those locations the processor may apply power to the release device 112 (e.g., the fan), and remove power when no longer at those locations or after a predetermined number of insects have been released, e.g., based on information received from one or more sensors arranged to detect insects exiting the insect storage 108 through an opening. Further, in some embodiments, the processor 102 may be configured to control the release device 112 and/or the loading mechanism 110 to release a substantially steady stream of insects. For example, embodiments disclosed herein may enable a substantially constant rate of release of insects, e.g., a set number of insects released per second, e.g., 1, 2, 3, 4, or 5 insects per unit of time (e.g., second) or per distance traveled (e.g., per a certain number of meters traveled by a vehicle on which the insect release system is mounted).

Advantages of Automated Mass Release of Insects

There are numerous advantages of automated mass release of insects. Embodiments described herein may allow for a system to be pre-programmed to release a set number of insects to be released in a specific area. Further embodiments described herein may allow for a steady stream of insects to be released at precise locations at precise times. For example, embodiments disclosed herein may enable a substantially constant rate of release of insects, e.g., a set number of insects released per second, e.g., 1, 2, 3, 4, or 5 insects per second. Embodiments described herein may be attached to a manned or an unmanned vehicle that then travels to an area so the insects can be released. Further, embodiments disclosed herein may enable accurate measurement and control of the number of insects released in an area. Some embodiments also reduce the risk of damage to the released insects, ensuring that a greater number of healthy insects are put into a habitat.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs including a sensor sampling routine, selection routines, and other routines to perform the methods described above.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A system comprising:
   a tube comprising a plurality of internal dividers defining one or more mosquito compartments;
   a loading mechanism configured to reposition the plurality of dividers and thereby reposition the one or more compartments to release mosquitos;
   a blower positioned to apply air pressure to a portion of the tube to force mosquitos to exit the tube; and
   a processor communicatively coupled to the loading mechanism and the blower and configured to control the loading mechanism and the blower.

2. The system of claim 1, wherein the loading mechanism further comprises a hopper comprising a plurality of tubes for storing mosquitos.

3. The system of claim 1, wherein the processor is coupled to one or more sensors and controls the blower based in part on signals received from the one or more sensors.

4. The system of claim 3, wherein the one or more sensors comprise a GPS receiver, and wherein the processor controls the blower based in part on a determined location.

5. The system of claim 3, wherein the one or more sensors comprise a sensor configured to measure a rate of release of mosquitos.

6. The system of claim 5, wherein the sensor configured to measure a rate of release of insects comprises one or more of: a camera, a microphone, an ultrasonic Doppler sensor, or a light sensor.

7. The system of claim 1, wherein the processor is configured to control the loading mechanism and the blower to release a stream of mosquitos.

8. The system of claim 1, wherein the tube, the loading mechanism, and the blower are mounted to a vehicle.

9. The system of claim 8, wherein the vehicle comprises one of: a car, a truck, a drone, a helicopter, or an airplane.

* * * * *

UNITED STATES PATENT AND TRADEMARK OFFICE
CERTIFICATE OF CORRECTION

PATENT NO. : 10,568,308 B2
APPLICATION NO. : 15/413564
DATED : February 25, 2020
INVENTOR(S) : Massaro et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 25 days.

Signed and Sealed this
Twenty-fourth Day of November, 2020

Andrei Iancu
*Director of the United States Patent and Trademark Office*